(12) United States Patent
Mutanen

(10) Patent No.: US 6,271,257 B1
(45) Date of Patent: Aug. 7, 2001

(54) DECREASING THE INTRACELLULAR LEVEL OF β-CATENIN BY ADMINISTERING HYDROXYMATAIRESINOL

(75) Inventor: Marja Mutanen, Helsinki (FI)

(73) Assignee: Hormos Nutraceutical Oy Ltd. (FI)

( * ) Notice: Subject to any disclaimer, the term of this patent is extended or adjusted under 35 U.S.C. 154(b) by 0 days.

(21) Appl. No.: 09/550,602

(22) Filed: Apr. 17, 2000

(51) Int. Cl.$^7$ ..................................................... A61K 31/00
(52) U.S. Cl. ........................... 514/461; 514/183; 514/449
(58) Field of Search ............................... 435/6, 91.1, 325, 435/375; 536/23.5, 24.33, 24.31, 23.1

(56) References Cited

U.S. PATENT DOCUMENTS 5,709,998 * 1/1998 Kinzler et al. ........................... 435/6
5,998,600 * 12/1999 Barker et al. ........................ 536/23.5

FOREIGN PATENT DOCUMENTS

WO 92/13103 * 8/1992 (WO) .

OTHER PUBLICATIONS

Mahmoud et al. Phenolic antioxidants modulate Apc function in vivo:Implications for colon cancer prevention. Proceeding of the American Association for Cancer Research Annual Meeting. vol. 40, pp. 530, Mar. 1999.*

Bras et al. Oxidative stress in familial adenomatous polyposis. European Journal of Cancer Prevention, vol. 8, No. 4, pp. 305–10, Aug. 1999.*

Saarinen et al. Hydroxymatairesinol, a Novel enterolactone precursor with antitumor properties from coniferous tree (picea abies). Nutrition and Cancer col. 36 No. 2. Abstract, Mar. 2000.*

Herter et al. Journal of Cancer Research and Clinical Oncology, vol. 125, No. 5, Abstract, 1999.*

* cited by examiner

*Primary Examiner*—John L. LeGuyader
*Assistant Examiner*—Janet Epps
(74) *Attorney, Agent, or Firm*—Rothwell, Figg, Ernst & Manbeck, p.c.

(57) ABSTRACT

The present invention relates to a method for decreasing the intracellular, especially nuclear level of β-catenin in an individual and to a method for the prevention or treatment of a disease or condition in an individual, wherein said disease or condition is related to a mutant APC gene or to an elevated level of intracellular β-catenin. Furthermore, the invention relates to methods for screening a subject to determine if said subject is a carrier of a mutant APC gene, and to methods for diagnosing an individual's predisposition for a disease or condition in an individual, said disease or condition being related to a mutant APC gene or to an elevated level of intracellular β-catenin.

2 Claims, 1 Drawing Sheet

DECREASING THE INTRACELLULAR LEVEL OF β-CATENIN BY ADMINISTERING HYDROXYMATAIRESINOL

FIELD OF THE INVENTION

This invention relates to a method for decreasing the intracellular, especially nuclear level of β-catenin in an individual and to a method for the prevention or treatment of a disease or condition in an individual, wherein said disease or condition is related to a mutant APC gene or to an elevated level of intracellular β-catenin. Furthermore, the invention relates to methods for screening a subject to determine if said subject is a carrier of a mutant APC gene, and to methods for diagnosing an individual's predisposition for a disease or condition in an individual, said disease or condition being related to a mutant APC gene or to an elevated level of intracellular β-catenin.

BACKGROUND OF THE INVENTION

The publications and other materials used herein to illuminate the background of the invention, and in particular, cases to provide additional detail with respect the practice, are incorporated by a reference.

Lignans are defined as a class of phenolic compounds possessing a 2,3-dibenzylbutane skeleton. They are formed by coupling of monomeric units called precursors such as cinnamic acid, caffeic, ferulic, coumaric, and gallic acids (Ayres and Loike, 1990). Lignans are widely distributed in plants. They can be found in different parts (roots, leafs, stem, seeds, fruits) but mainly in small amounts. In many sources (seeds, fruits) lignans are found as glycosidic conjugates associated with fiber component of plants. The most common dietary sources of mammalian lignan precursors are unrefined grain products. The highest concentrations in edible plants have been found in flaxseed, followed by unrefined grain products, particularly rye.

Considerable amounts of lignans are also found in coniferous tree. The type of lignans differs in different species and the amounts of lignans vary in different parts of the trees. The typical liguans in heart wood of spruce (*Picea abies*) are hydroxymatairesinol (HMR), α-conidendrin, conidendrinic acid, matairesinol, isolariciresinol, secoisolariciresinol, liovile, picearesinol, lariciresinol and pinoresinol (Ekman 1979). The far most abundant single component of lignans in spruce is HMR, about 60 percent of total lignans, which occurs maninly in unconjugated free form. Lignan concentration in thick root is 2–3 percent. Abundance of lignans occur in the heart wood of branches (5–10 percent) and twists and especially in the knots, where the amount of lignans may be higher than 10 percent (Ekman, 1976 and 1979). These concentrations are about hundred-fold compared to ground flax powder known as lignan-rich material.

The chemical structure of hydroxymatairesinol is represented by the formula

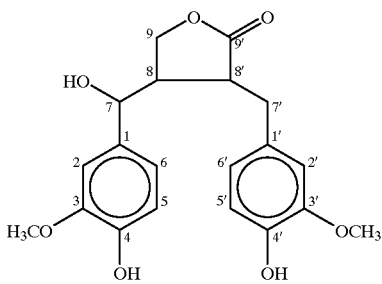

As an experimental evidence for the chemopreventive actions of lignans, supplementation of a high-fat diet with lignan-rich flaxseed flour (5% or 10%) or flaxseed lignans (secoisolariciresinol-diglycoside, SDG) inhibited the development of antiestrogen-sensitive dimethylbenzanthracene (DMBA)-induced breast cancer in the rat (Serraino and Thompson 1991 and 1972; Thompson et al, 1996a and 1996b). They reduced the epithelial cell proliferation, nuclear aberrations, the growth of tumors, and the development of new tumors. High lignan intake may also protect against experimental prostate and colon cancers.

Germline mutations of adenomatous polyopsis coli (APC) gene may lead to Familial Adenomatous Polyposis (FAP) syndrome. In FAP syndrome, the aberrant function of APC-gene is considered to be an important initiation event for the development of sporadic adenomas in animals and in humans (Fearon et al, 1990; Groden et al, 1991; Herter et al, 1999). APC is a tumor suppressor gene located in chromosome 5q21. APC mutation is a very early event in the development of FAP. It occurs already before ras mutations (Powell et al, 1992) and is suggested to be, together with other mutations, a risk factor for colorectal cancer. There is no specific treatment for FAP.

The APC-gene encodes a cytoplasmic that can bind to and promote the degradation of β-catenin, which plays a dual role in the cell. One role is linking the cytoplasmic side of cadherin-mediated cell-cell contacts to the actin cytoskeleton, and the other is the abiltiy to bind members of the Tcf-family of transcription factors and activate mostly unknown target genes. The target genes most likely involve c-myc, cyclin D1, c-jun and fra-1 that are the components of AP-1, uPAR and PPARδ. Mutations of APC cause aberrant accumulation of β-catenin, which alter the expression of above-mentioned genes. Currently it is assumed that overexpression of β-catenin, which is caused by lack of APC gene function, results in abnormal gene transcription, which promotes the development of benign adenomas, polyps and possibly malignant tumors.

An animal model, which resembles to human FAP syndrome, and which is considered to be the best experimental model for human FAP, is the mouse with APC$^{min}$ mutation bearing a heterozygous nonsense mutation at codon 850 of the APC gene. The codon 850 is located at the mutation cluster region, which is the most often mutated region of the APC gene in human colon cancer (Peifer & Polakis, 2000). APC$^{min}$ mice develop sporadic adenomas in different parts of the gut. The intracellular distribution of β-catenin in the adenomas is cytoplasmic and nuclear when compared to mainly membraneous distribution in non-mutated mice. Similar β-catenin distribution is seen in many human cancers and apc-mutation is considered to be the principal cause of the phenomenon.

The results of the present study indicate that levels and distribution β-catenin can be regulated by HMR. Futher, the number of adenomas in the experimental mouse model can be decreased by HMR. Thus, HMR can be used for the prevention and treatment of FAP and other diseases which are characterized by elevated level of β-catenin and its nuclear distribution.

SUMMARY OF THE INVENTION

According to one aspect, this invention concerns a method for decreasing the intracellular level of β-catenin in an individual, comprising administering to said individual an effective amount of hydroxymatairesinol or a geometric isomer or steroisomer thereof.

According to another aspect, the invention concerns a method for the prevention or treatment of a disease or condition in an individual, said disease or condition being related to a mutant APC gene, or to an elevated level of intracellular β-catenin, said method comprising administering to said individual an effective amount of hydroxymatairesinol or a geometric isomer or stereoisomer thereof.

According to a third aspect, the invention concerns a method for screening a subject to determine if said subject is a carrier of a mutant APC gene, comprising the steps of
providing a biological sample of the subject to be screened; and
providing an assay for detecting in the biological sample the presence of i) the normal APC gene or II) the mutant APC gene.

According to a fourth aspect, the invention concerns a method for diagnosing an individual's predisposition for a disease or condition in an individual, said disease or condition being related to a mutant APC gene, or to an elevated level of intracellular β-catenin, said method comprising determining whether said individual has a mutant APC gene, according to the screening method mentioned above.

DETAILED DESCRIPTION OF THE INVENTION

Figure 1:
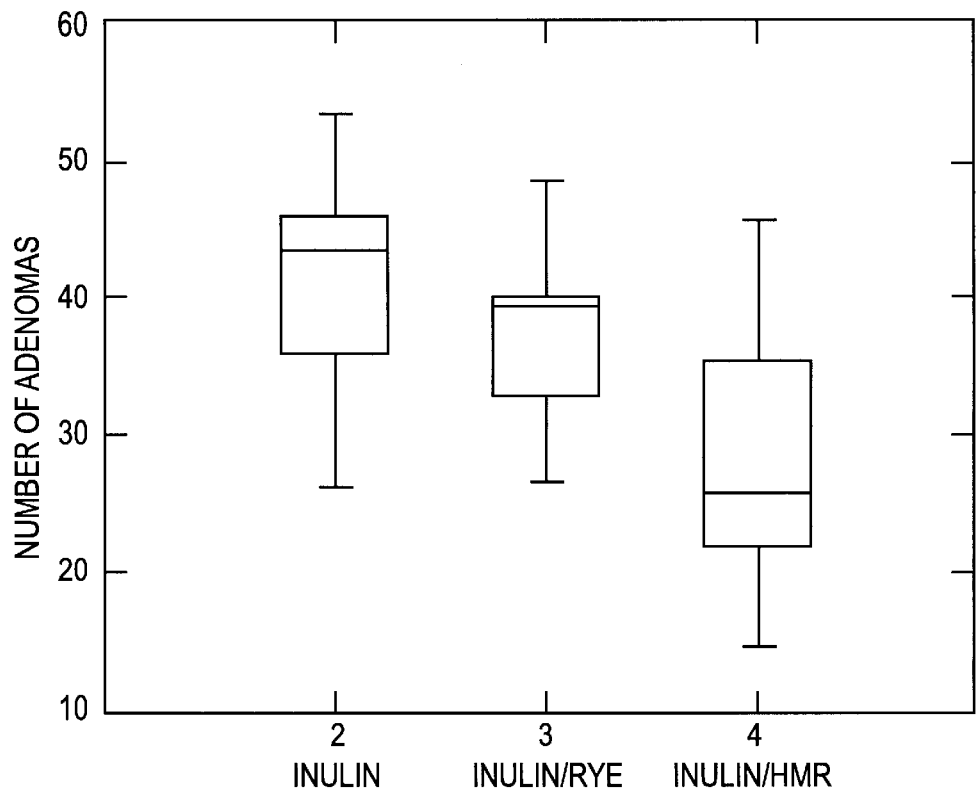
FIG. 1 shows the total number of adenomas as box-blots in the small intestine of $Apc^{Min}$ mice fed for five weeks with high fat diet supplemented either with 2.5% of inulin (A), 2.5% of inulin and 10% of rye bran (B) or 2.5% of inulin and 0.02% of hydroxymatairesinol (HMR) (C). P<0.05 between HWR and other two diet-groups (Mann-Whitney U test).

This invention relates to the use of HMR as a therapeutically active compound particularly in diseases, where β-catenin distribution in the cells is abnormal, i.e. maily cytosolic and/or nuclear. In humans such condition is typically seen as familial disease known as familial adenomatous polyposis (FAP). This condition may be herediatary, but similar conditions may also occur due to environmental factors, which are only poorly known. The animal model, apc-min mutation mouse model, used in this invention, resembles this human condition.

β-catenin is one of the proteins, which are linked to the communication of cells with each other. On the other hand, if it is mutated, like in intestinal polyposis, or if it is distributed to cytosolic or nuclear compartments, it may induce cell proliferation and thus promote adenoma development.

For the purpose of this invention, HMR or its naturally occurring isomers can be administered by various routes. The suitable administration forms include, for example, oral formulations, parenteral injections including intravenous, intramuscular, intradermal and subcutaneous injection; and transdermal or rectal formulations. In addition, HMR can be administered as a part of functional food or food incredient or food additive. Suitable oral formulations for pharmaceutical purposes include e.g. conventional or slow-release tablets and gelatine capsules.

The required dosage of HMR will vary depending on the disease or condition to be treated. For FAP, it depends on the adenoma properties and the stage and metastatic dissemination. HMR can be administered preferable once or twice daily. The daily dose is 5–100 mg, preferably 30–80 mg daily. HMR can be given as tablets or other formulations like gelative capsules alone or mixed in any clinically acceptable non-active ingredients, which are used in the pharmaceutical industry. In addition, HMR can be administered mixed in different food constituents or can be administered as functional food.

The invention, the use of HMR in the treatment of FAP and other diseases, can be applied based on clinical conditions and symptoms. The exploitation of the invention can also be based on the diagnosis of apc-mutation in each subject by using individual DNA mutation assays, or on the diagnosis of β-catenin distribution by polyclonal or monoclonal antibodies against β-catenin or parts of this protein.

The DNA sequence or the mutant APC gene can be used for screening a subject to determine if said subject is a carrier of a mutant APC gene. The determination can be carried out either as a DNA analyse according to well known methods, which include direct DNA sequencing of the normal and mutated APC gene, allele specific amplification using the polymerase chain reaction (PCR) enabling detection of either normal or mutated APC sequence, or by indirect detection of the normal or mutated APC gene by various molecular biology methods including e.g. PCR-single stranded conformation polymorphism (SSCP)-method or denaturing gradient gel electrophoresis (DGGE). Determination of the normal or mutated APC gene can also be done by using restriction fragment length polymorphism (RFLP)-method, which is particularly suitable for genotyping large number of samples.

The determination can also be carried out at the level of RNA by analysing RNA expressed at tissue level using various methods. Allele spesific probes can be designed for hybridization. Hybridization can be done e.g. using Northern blot, RNase protection assay or in situ hybridization methods. RNA derived from the normal or mutated APC gene can also be analysed by converting tissue RNA first to cDNA and thereafter amplifying cDNA by an allele spefic PCR-method and carrying out the analysis as for genomic DNA as mentioned above.

Alternatively, the determination can be carried out as an immunohistochemical method where a sample is contacted with an antibody capable of binding β-catenin or a fragment thereof. An elevated level of intracellular, particularly nuclear, β-catenin is used as an indication of the occurrence of the mutated APC gene or β-catenin gene.

The production of antibodies can be done in experimental animals in vivo to obtain polyclonal antibodies or in vitro using cell lines to obtain monoclonal antibodies.

The invention will be described more in detail in the following Experimental Section.

EXPERIMENTS

The Laboratory Animal Ethics Committee of the Faculty of Agriculture and Forestry, University of Helsinki approved the study protocol. Male C57BL/6J-Min (multiple intestinal neoplasia) mice, 5–6 weeks of age, were obtained from the Jackson Laboratory, (Bar Habor, Me., USA). The animals were stratified by body mass and age and assigned randomly to the experimental diets, 8 mice/group, with initial body mass of 21.5 g. Animals were housed in plastic cages in a temperature- and humidity-controlled animal facility, with 12-h light/dark cycle. They had a free access to the semi-synthetic diets and tap water for five to six weeks. The body weights of the animals were recorded weekly.

The high fat (40-energy %) experimental diets were composed in a way that the diets contained similar amounts of protein, carbohydrate and fat per energy (Table 1). The fat used in the diets was a mixture of butter, rapeseed oil, and sunflower seed oil providing the intake of saturated, monounsaturated and polyunsaturated fatty acid in the ratio 3:2:1. It corresponded the intake of these fatty acids in the Western type diet. All diets contain 2.5% (w/w) polydisperse $\beta(2\rightarrow1)$ fructan, inulin (Raftiline®,Orafti, Tienen, Belgium). The rye bran-supplemented diet was prepared by diluting the fiber-free high-fat diet with addition of rye bran at 100 g/kg diet. In this way the nutrient intake per energy was kept constant in all diets. HMR was stored on +4° C. in darkness prior to use. The diets were stored at −20° C. and kept at 4° C. only for the use within one week.

After the feeding period, the mice were killed by $CO_2$ asphyxiation. The small intestine, caecum and colon were removed, open along the longitudinal axis and rinsed with ice-cold saline. The small intestine was divided into five sections. The caecum and colon were kept together. The small intestine and colon+caecum were then spread flat on a microscope slide and a number; diameter and location of adenomas were determined with an inverse light microscope with a screen at a magnification of ×2.5. The diameter of adenomas was scored with a mm-scale placed on the screen.

The adenomas from each section of the intestine were clipped off as well as the mucosa was scraped off with a microscope slide and snap frozen in liquid nitrogen. Tissue samples were homogenized, and the cytosol and particulate fractions extracted as described previously (A-M Pajari et al., 1998) with the addition of the extra centrifugation (8 500×g for 10 min at 4° C.) to get the nuclear fraction. Rat brain homogenate was used as positive control for $\beta$-catenin in immunoblotting analysis.

For immunoblotting analysis, 5 ml of the crude extracts were concentrated to 1/50 volume with Millipore Ultrafree®-4 tubes (Millipore, Bedford, Mass.). After protein concentration measurement (Bradford, Bio-Rad protein assay reagent) the homogenate was mixed with equal volume of SDS sample buffer, boiled for 5 min and stored at −80° C. until use.

Samples (30 µg) and rat brain homogenate (10 µg) were subjected to 10% SDS-PAGE and then transferred to polyvinylidene difluoride (PVDF) membranes (Bio-Rad Laboratories, Hercules, Calif.) at 210 mA for 2h. The membranes were blocked at 4° C. overnight with 1% nonfat dry milk in phosphate-buffered saline (PBS), washed with 0.5% BSA in PBS, incubated with monoclonal mouse anti-$\beta$-catenin antibody (Transduction Laboratories, Lexington, Ky.) and alkaline phosphatase-conjugated anti-mouse secondary antibody (Zymed, San Francisco, Calif.) in 1% BSA in PBS. $\beta$-Catenin antibody dose not recognize other catenins. Monoclonal mouse anti-$\beta$-catenin from Santa Cruz Biotechnology (Santa Cruz, Calif.) was used to confirm the specificity of the $\beta$-catenin signal. $\beta$-Catenin bands were visualized by colorimetric staining with 5-bromo-4-chloro-3-indolyl phosphate and nitroblue tetrazolium substrate mix (Bio-Rad Laboratories,Hercules,Calif.). Blots were scanned and analyzed on a Sharp JX325 Scanner with ImageMaster®1D Software, version 2 (Pharmacia Biotech, Uppsala, Sweden). Results in duplicates are expressed as sample band intensity (optical density of the $\beta$-catenin band multiplied by band area) divided by rat brain band intensity.

The differences between the groups were analyzed by non-parametric Mann-Whitney U test (SPSS Inc., version 6.1). Data were considered significant at P<0.05.

RESULTS

In recent years, considerable efforts have been made to either synthesize or find natural agents that are able to arrest or reverse carcinogenic processes, and thus prevent cancer. In this study, we tested the possible chemopreventive effect of HMR on intestinal adenoma development in $Apc^{Min}$ mice, an animal model of human Familial Adenomatous Polyposis (FAP). HMR showed a strong chemopreventive effect in our study by especially preventing the formation of new intestinal adenomas, which was seen as a significantly lower number of adenomas in the mice fed HMR compared with the mice fed the other diets. The mean number of adenomas in the small intestine was only 26.6±11.0 (mean±SD) in mice fed HMR while it was 39.6±8.9 (P=0.031 compared to HMR group) in inulin fed mice and 36.0±7.4 (P=0.049 compared to HMR group) in inulin/rye fed mice (FIG. 1). HMR did not affect the growth of existing adenomas since there were no differences in mean diameter, adenoma size (% of total), and distribution of adenomas along the length of the intestine between the diet groups. In the colon and caecum, the incidence of adenomas (60–75%) and the number of adenomas (0.9–1.3) did not differ between the groups.

Figure 2:
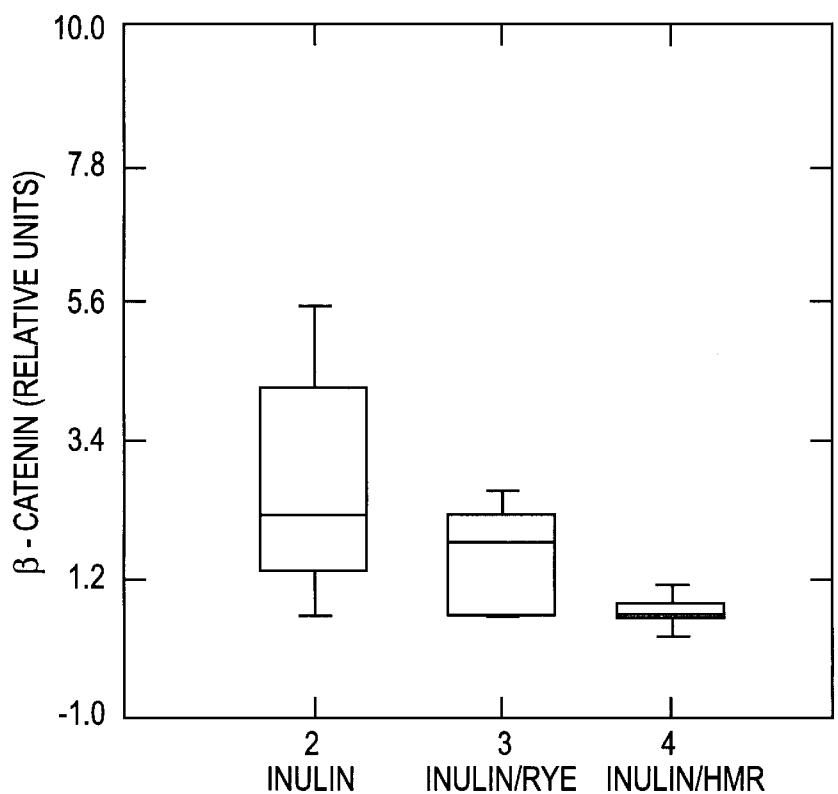
FIG. 2 shows the nuclear β-catenin level of the adenoma tissue as box-blots of $Apc^{Min}$ mice fed for five weeks with high fat diet supplemented either with 2.5% of inulin (A), 2.5% of inulin and 10% of rye bran (B) or 2.5% of inulin and 0.02% of hydroxymatairesinol (HMR) (C). P<0.05 between HMR and other two diet-groups (Mann-Whitney U test).

HMR resulted in normalization of $\beta$-catenin levels in adenoma tissue of $Apc^{Min}$ mice, indicating that HMR mediates its chemopreventive effect through the Apc-$\beta$-catenin pathway. Wild type Apc protein regulates intracellular $\beta$-catenin level and prevents the entrance of $\beta$-catenin into the nucleus where excess $\beta$-catenin could tiger abnormal gene transcription (V Korinek et al., 1997; PJ Morin et al., 1997; J Beherens et al., 1996). We measure $\beta$-catenin levels in cytosolic, particulate and nuclear fractions of both adenoma and surrounding mucosa tissues in the small intestine (Table 2). In the cytosolic fraction, $\beta$-catenin level in adenoma tissue was significantly elevated (P=0.008–0.013) in all the diet groups as compared to that of the surrounding mucosa. In the nuclear fraction, $\beta$-catenin in the inulin and inulin/rye groups was also significantly higher (P=0.003–0.009) in the adenoma tissue when compared to the surrounding mucosa. However, HMR was able to restore nuclear $\beta$-catenin level of the adenoma tissue to the level found in the surrounding mucosa (FIG. 2, Table 2). Since there was also a tendency if cytosolic $\beta$-catenin to be low in HMR fed mice, it can be speculated that HMR might both enhance degradation of cytosolic $\beta$-catenin and prevent $\beta$-catenin transport to the nucleus.

Originally our aim was to see whether HMR and rye (i.e. matairesinol) have a similar chemopreventive effect on inulin promoted adenoma formation in $Apc^{Min}$ mice. Even though HMR was quite potent in this respect, rye was not able to overcome the adenoma promotive effect of inulin. One reason for this may be the huge difference in the concentrations of HMR and matairesinol in the diets. Estimated intake of HMR was about 20 mg/kg bwt daily and that of matairesinol about 17 µg/kg bwt daily. The exact chemopreventive mechanism of HMR needs further clarification. So far HMR has been shown to be protective in two different studies: in addition to our study with Apc$^{Min}$ mice, HMR has protected against DMBA-induced mammary tumors in rat (N Saarien et al., in press). Although lignans are classified as phytoestrogens, HMR do not have estrogenic, antiestrogenic or antiandrogenic activity in rats (N Saarien et al., in press).

The question of safety is important when looking for new chemopreventive compounds. In our study no differences in body weight gain were found between the groups during the course of the experiment. The final body weight (g) of the animals were 30, 30 and 31.5 for the inulin, inulin/rye and inulin HMR diet groups, respectively, indicating that the animals grew well.

TABLE 1

Nutrient composition of experimental diets (g/kg diet)[a]

| Ingredient | Inulin 2.5% and Inulin 2.5% + HMR | Inulin 2.5% + Rye Bran 10% |
|---|---|---|
| Energy (kcal/100 g) | 475 | 430 |
| Casein | 229.9 | 2073 |
| Dextrose | 466.1 | 420.2 |
| Butter | 145.0 | 130.6 |
| Sunflower oil | 3.0 | 11.6 |
| Rapeseed oil | 60.6 | 54.5 |
| Mineral mix (AIN-93-M-MX) | 40.4 | 36.4 |
| Vitamin mix (AIN-93-VX) | 1.5 | 10.2 |
| L-cystine | 3.5 | 3.1 |
| Colinechloride | 3.5 | 3.1 |
| BHQ | 0.014 | 0.014 |
| HMR[b] | 0.2 | — |
| Inulin (Raftiline ®, Orafti) | 25.0 | 25.0 |
| Rye Bran | — | 100.0 |

[a]Casein was obtained from Kainuun Osuusmeijeri (Sotkamo, Finland), dextrose from Six Oy (Helsinki, Finland), mineral and vitamin mix from Harlan Teklad (Madison, WI), L-cystine, Cholinechloride and tertiary butylhydroxyquinone from Yliopiston Apteekki (Helsinki, Finland). Inulin (Raftiline ®) was from Orafti (Tienen, Belgium), HMR from Hormos Medical Ltd, Turku and rye bran from Melia (Finland). Butter, sunflower oil, and rapeseed oil were from a local market.
[b]the purity of the HMR fraction was about 47%.
[c]contain 100–150 µg matairesinol/per 100 g dry weight (2).

TABLE 2

β-catenin expression in the distal small intestine of Min mice on the inulin, inulin/rye and inulin/HMR diets (relative units[a]), mean ± SD

| Group | Tissue | cytosol | particulate | nuclear | total* |
|---|---|---|---|---|---|
| Inulin | Adenoma | 2.93 ± 1.57 | 2.43 ± 1.54 | 3.15 ± 2.90 | 8.56 ± 4.31 |
| | Mucosa | 1.24 ± 0.79[b] | 1.27 ± 0.89 | 0.50 ± 0.50[b] | 3.1 ± 2.06[b] |
| Inulin/rye | Adenoma | 2.33 ± 1.36 | 2.85 ± 2.54 | 5.17 ± 6.94 | 9.71 ± 8.38 |
| | Mucosa | 0.90 ± 0.59[b] | 1.45 ± 0.33 | 0.35 ± 0.39[b] | 2.67 ± 2.12[b] |
| Inulin/HMR | Adenoma | 1.78 ± 0.66 | 3.26 ± 3.13 | 0.41 ± 0.25[c] | 5.45 ± 3.38 |
| | Mucosa | 0.88 ± 0.49 | 1.19 ± 1.17 | 0.36 ± 0.28 | 2.42 ± 1.76 |

*total = cytosol + particulate + nuclear
[a]Results in duplicates are expressed as sample band intensity (optical density of the β-catenin band mulitplied by band area) divided by rat brain band intensity.
[b]$p < 0.05$ compared with the adenoma tissue within a diet group (Mann-Whitney U test)
[c]$p < 0.05$ compared with inulin and inulin/rye dites (Mann-Whitney U test)

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Ayres D, and Loike, J. Lignans: Chemical, biological and clinical properties. Cambridge University press, 1990.

Ekman R: Analysis of lignans in Norway spruce by combined gas chromatography-mass spectrometry. Holzforschung, 30:79–85, 1976.

Ekman R: Distribution of lignans in Norway spruce. Acta Academiae Aboensis, Ser B, 39:1–6, 1979.

Serraino M and Thompson LU: The effect of flaxseed supplementation on early risk markers for mammary carcinogenesis. Cancer Letters, 60: 135–142, 1991.

Serraino M and Thompson LU: The effect of flaxseed supplementation on the initiation and promotional stages of mammary tumorigenesis. Nutr Cancer, 17:153–159, 1992.

Thompson LU, Seidl, MM, Rickard SE, Orcheson, LJ, and Fong HHS: Antitumorigenic effect of a mammalian lignan precursors from flaxseed. Nutr Cancer, 26: 159–165, 1996a.

Thompson LU, Rickard SE, Orcheson LJ and Seidl MM: Flaxseed and its lignan and oil components reduce mammary tumor growth at a late stage of carcinogenesis. Carcinogenesis, 17: 1373–1376, 1996b.

Fearon, ER & Vogelstein BA. A genetic model for colorectal tumorigenesis. Cell 61;759–767, 1990.

Groden J, Thliveris A, Spirio L, et al. Identification and characterization of the familial adenomatous polyposis coli gene. Cell 66;689–600, 1991.

Herter P, Kuhnen C, Müller K-M, Wittinghofer A, Müller O: Intracellular distribution of β-catenin in colorectal adenomas, carcinomas and Peutz-Jeghers polyps. J Cancer Res Clin Oncol 125:297–304,1999

Powell SM, Zilz N, Beazer-Barclay Y, Bryan TM, Hamilton SR, Thibodeau SN, Vogelstein B, Kinzler KW: APC mutations occur early during colorectal tumorigenesis. Nature 259:235–237, 1992

N. Saarinen, A. Wärri, S. Mäkelä, C. Eckerman, M. Reunanen, M. Ahotoupa, S. Salmi, A. A. Franke, L. Kangas, R. Santti, Hydroxymatairesinol, a novel enterolactone precursor with antitumor properties from coniferous tree (*Picea Abies*), Nutr Cancer, (in press).

A-M. Pajari, P. Häkkänen, R-D. Duan, M. Mutanen, Role of red meat and arachidonic acid in protein kinase c activation in rat colonic mucosa., Nutr Cancer 32 (1998) 86–94.

V. Korinek, N. Barker, P. J. Morino, D. van Wichen, R. de Weger, K. W. Kinzler, B. Vogelstein, H. Clevers, Constitutive transcriptional activation by b-catenin-Tcf-complex in APC -/- colon carcinoma, Science (Washington D.C.) 275 (1997)1784–1787.

P. J. Morin, A. B. Sparks, V. Korinek, N. Barker, H. Clevers, B. Vogelstein, K. W. Kinzler, Activation of b-catenin-Tcf-signaling in colon cancer by mutations in b-catenin or APC, Science 275 (1997)1787–1789.

J. Beherens, J. P. von Kries, M, Kühl, L. Bruhn, D. Wedlich, R. Grosschedl, W. Birchmeire, Functional interaction of b-catenin with the transcription factor LEF-1, Nature 382 (1996) 638–642.

M. Peifer, P. Polakis, Wnt signaling in oncogenesis and embryogenesis—a look outside the nucleus. Science 287 (2000) 1606–1609.

What is claimed is:

1. A method for treating an individual having Familial Adenomatous Polyposis (FAP), comprising administering to said individual an effective amount of hydroxymatairesinol wherein the intracellular level of $\beta$-catenin protein in said individual is decreased.

2. A method for treatment of a disease or condition in an individual, said disease or condition being related to a mutant APC (adenomatous polyposis coli) gene, or to an elevated level of intracellular $\beta$-catenin, said method comprising administering to said individual an effective amount of hydroxymatairesinol wherein said disease or condition is FAP.

* * * * *